(12) United States Patent
Hassanali et al.

(10) Patent No.: US 8,734,773 B2
(45) Date of Patent: May 27, 2014

(54) COMPOSITIONS FOR ATTRACTING BLOOD-FEEDING INSECTS

(75) Inventors: Ahmed Hassanali, Nairobi (KE); Isaiah Ndiege, Nairobi (KE); Maurice Vincent Omolo, Nairobi (KE); Basilio Ngari Njiru, Nairobi (KE); Peter G. N. Njagi, Nairobi (KE)

(73) Assignees: International Centre of Insect Physiology and Ecology, Nairobi (KE); Kenyatta University, Nairobi (KE)

( * ) Notice: Subject to any disclaimer, the term of this patent is extended or adjusted under 35 U.S.C. 154(b) by 91 days.

(21) Appl. No.: 13/377,131

(22) PCT Filed: Jun. 8, 2010

(86) PCT No.: PCT/KE2010/000021
§ 371 (c)(1),
(2), (4) Date: Dec. 8, 2011

(87) PCT Pub. No.: WO2010/143752
PCT Pub. Date: Dec. 16, 2010

(65) Prior Publication Data
US 2012/0082639 A1 Apr. 5, 2012

(30) Foreign Application Priority Data
Jun. 11, 2009 (KE) .................... KE/P/2009/000922

(51) Int. Cl.
A01N 35/02 (2006.01)
A01N 37/02 (2006.01)
A01N 31/08 (2006.01)

(52) U.S. Cl.
USPC ........................................ 424/84

(58) Field of Classification Search
CPC ....... A01N 35/02; A01N 37/02; A01N 31/08; A01N 2300/00
USPC ........................................ 424/84
See application file for complete search history.

(56) References Cited

U.S. PATENT DOCUMENTS 4,152,422 A * 5/1979 Ohinata et al. .................. 424/84
2007/0202141 A1 * 8/2007 Jumean et al. ................ 424/416

FOREIGN PATENT DOCUMENTS

GB 2388544 * 11/2003 ............. A01N 35/06

OTHER PUBLICATIONS

Bernier et al. ("Analysis of Human Skin Emanations by Gas Chromatography/Mass Spectrometry. 1. Thermal Desorption of Attractants for the Yellow Fever Mosquito (*Aedes aegypti*) from Handled Glass Beads", Analytical Chemistry, 1999, 71(1), 1-7).*

* cited by examiner

*Primary Examiner* — Kortney L Klinkel
(74) *Attorney, Agent, or Firm* — Isaac Rutenberg

(57) ABSTRACT

Methods and compositions suitable for influencing insect behavior are provided. In a preferred embodiment, the compositions comprise a blend of between two and eight insect attractant compounds selected from the group consisting of: a) compounds of formula (I); b) compounds of formula (II); c) compounds of formula (III). Wherein: n is zero or an integer; x is zero or an integer selected from 1-8, or greater than 9; and R is a $C_1$-$C_{12}$ alkyl. The compositions are useful as bait, with or without other mammalian body odor constituents or synthetic attractants, to attract disease carrying insects to traps or targets.

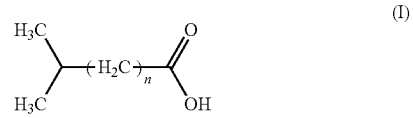

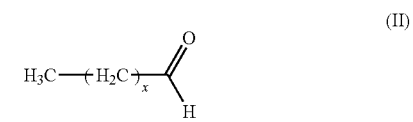

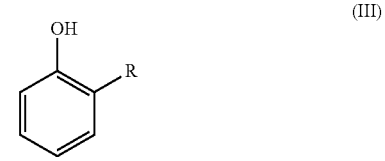

21 Claims, No Drawings

COMPOSITIONS FOR ATTRACTING BLOOD-FEEDING INSECTS

TECHNICAL FIELD

This invention relates to compositions suitable for controlling the behaviour of insects, as well as methods of use of such compositions. The invention finds utility, for example, in the field of disease control.

BACKGROUND

Mosquitoes are important vectors of several tropical diseases, including malaria, filariasis, and a series of viral diseases such as dengue, Japanese encephalitis, West Nile virus, and yellow fever. Of these, malaria-transmitting species are highly important. Globally, an estimated 200-300 million people are affected by malaria, of which 1.5-2.7 million die each year. Over 90% of these cases occur in sub-Saharan Africa and children under-five years are worst hit by the disease. The burden malaria imposes on the economy is substantial. The high morbidity and mortality in some countries with intense transmission has reduced annual per capita income by up to 1.3%. In fact, a 10% reduction in malaria has been associated with 0.3% higher growth in economy. Many man-hours are lost each day from those suffering from malaria or looking after such patients. Pregnant women infected with malaria suffer severe anaemia with up to 800,000 infantile mortalities, a substantial number of miscarriages, and very low birth weight babies, annually. In addition, the spread of drug resistant malaria strains substantially raises the cost of treatment.

Malaria is transmitted by *Anopheles* mosquitoes. Of about 380 species around the world, some 60 species are sufficiently attracted to humans to act as vectors of malaria. Most cases of the disease in sub-Saharan Africa are transmitted by *An. gambiae* Giles complex and *An. funestus* Giles that are strongly attracted to human hosts (i.e. are highly anthropophilic). Control of the disease is through chemotherapy, chemoprophylaxis and vector control. Vector control includes environment management, biological control, use of insecticides for adult and larval control, and personal protection (e.g. using repellents and mosquito nets). Chemical-based methods of vector control focus largely on repellant compounds and compositions. Unfortunately, the use of chemical repellants frequently requires widespread application of chemicals. In addition, many repellants are associated with adverse medical side effects. For example, N.N-diethyl-meta-toluamide (DEET) is a widely used mosquito repellant that, unfortunately, has been identified as an irritant and is known to cause allergic reactions, seizures, and other conditions.
unfortunately, has been identified as an irritant and is known to cause allergic reactions, seizures, and other conditions.

The use of attractants in vector control has received much less attention compared with the use of repellents, in part because of a lack of candidates that are sufficiently attractive to the targeted insects. Carbon dioxide present in the expired breath of mosquito hosts is the best known olfactory stimulant of mosquitoes. Other known host odour constituents include 1-octen-3-ol, lactic acid, 4-methylphenol, and fatty acids associated with activity of microflora present on host skin. However, none of these with or without $CO_2$ account for the strong attraction of Afrotropical malaria vectors to their preferred hosts. A review of the effects of various host odours can be found, for example, in Takken et al., "Odor-Mediated Behavior of Afrotropical Malaria Mosquitos," *Annu. Rev. Entomol.* (1999) 44:131-157.

An ideal method for controlling mosquito and other blood-feeding insect populations would incorporate insect attractive compositions. Such insect attractant compositions would ideally contain readily available compounds that are non-toxic at insect-attractant concentrations.

SUMMARY OF THE INVENTION

The present invention is directed at addressing one or more of the abovementioned drawbacks, as well as similar issues pertaining to control of insects and insect behaviour.

In one aspect of the present invention, therefore, there is provided a composition for modifying insect behaviour. The composition comprises at least two but not more than eight insect attractant compounds selected from: (a) compounds having the structure of formula (I)

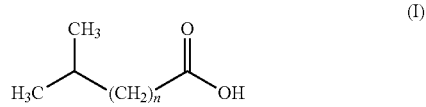

wherein n is zero or an integer;
(b) compounds having the structure of formula (II)

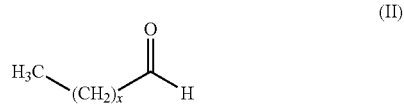

wherein x is zero or an integer selected from 1-8 or greater than 9; and
(c) compounds having the structure of formula (III)

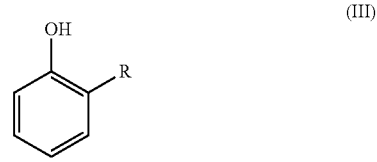

wherein R is $C_1$-$C_{12}$ alkyl.

In another aspect, the invention provides a method for controlling insects. The method comprises preparing an insect attractant composition by selecting at least two compounds found in compositions associated with human odours, selecting a relative amount for each compound, and combining the compounds in the selected amounts to provide an insect attractant composition. In one example, the at least two compounds have the structure of formula (I), (II), or (III).

In a further aspect, the invention provides a method for controlling the behaviour of insects. The method comprises: (a) preparing an insect-attractive composition comprising at least two compounds selected from compounds having the structure of formula (I), formula (II), and formula (III); and (b) supplying the composition to an environment containing insects.

In a still further aspect, the invention provides a composition comprising between two and eight compounds selected from compounds having the structure of formula (I), formula (II), and formula (III), wherein the composition is attractant to mosquitoes, and further wherein the composition does not contain any insect repellant compounds.

DETAILED DESCRIPTION OF THE INVENTION

Unless otherwise indicated, the invention is not limited to specific procedures, starting materials, or the like, as such may vary. It is also to be understood that the terminology used herein is for the purpose of describing particular embodiments only and is not intended to be limiting.

In describing and claiming the present invention, certain terminology will be used in accordance with the definitions set out below.

As used herein, the phrase "having the formula" or "having the structure" is not intended to be limiting and is used in the same way that the term "comprising" is commonly used.

The term "alkyl" as used herein refers to a branched or unbranched saturated hydrocarbon group (i.e., a mono-radical) typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term "lower alkyl" intends an alkyl group of 1 to 6 carbon atoms. "Substituted alkyl" refers to alkyl substituted with one or more substituent groups, including instances wherein two hydrogen atoms from the same carbon atom in an alkyl substituent are replaced, such as in a carbonyl group. The terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

Substituent groups include, for example, alkyl groups such as $C_1$-$C_{12}$ alkyl, or $C_1$-$C_6$ alkyl, or $C_1$-$C_3$ alkyl groups. Preferred substituents include, for example, methyl, ethyl, n-propyl, isopropyl, n-butyl, isobutyl, t-butyl, octyl, decyl, cyclopentyl, cyclohexyl, and the like.

As used herein, the term "insect attractive" refers to a compound or composition that, when present in an environment containing insects, either alone or in combination with other compounds, tends to cause insects to be drawn toward areas of higher concentrations of the compound or composition.

As used herein, the term "insect repellant" refers to a compound or composition that, when present in an environment containing insects, either alone or in combination with other compounds, tends to cause insects to be driven away from areas of higher concentrations of the compound or composition.

As used herein, the term "composition" refers to a substance containing at least two distinct chemical compounds. For example, a composition may contain an active compound and an additive such as a carrier, or a composition may contain two active compounds with or without a carrier. The term "blend" refers to a substance containing at least two active compounds.

As used herein, the term "active compound" refers to a compound that, either alone or in combination with other compounds, elicits a behavioral change in insects.

In one aspect, the invention provides methods and compositions suitable for controlling insect behaviour. In preferred embodiments, suitable compositions are blends of two or more active compounds selected from naturally occurring, insect attractant compounds.

In some preferred embodiments, suitable compounds are insect attractant compounds found in naturally occurring compositions associated with animal odours. Suitable compositions are blends of two or more active compounds selected from insect attractant compounds found in naturally occurring compositions associated with animal odours.

Naturally occurring compositions associated with animal odours are compositions that may result from biological processes such as respiration, perspiration, and the action of microflora on human skin. For example, such compositions may be odor compounds that are associated with humans. Particularly preferred are human foot odours. It will be appreciated, then, that the phrase "human foot odour" is meant to include compounds that are naturally found on the foot of a human host, and that may be produced by the human host (e.g., via perspiration) or by microflora residing on the human host.

It will be appreciated that each individual active compound of the compositions described herein may or may not have inherent insect attractant properties. Furthermore, the overall attractiveness of a composition may be greater than the summation of the attractiveness for each individual compound. That is, the compositions of the invention exhibit synergistic effects.

In some embodiments, the methods of insect control according to the invention involve compounds having the structure of formula (I)

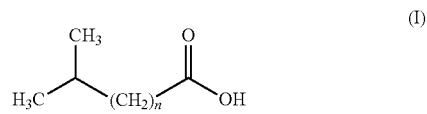

wherein n is an integer. For example, n may be between 0 and 10, or between 0 and 4, or n may be 0, 1, 2, 3, 4, 5, 6, 7, 8, 9, 10, 11, 12, 13, or 14. In certain preferred embodiments, n is selected from 0, 1, and 2.

In some embodiments, the methods of insect control according to the invention involve compounds having the structure of formula (II)

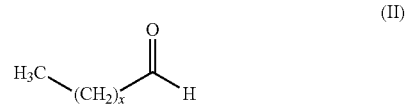

wherein x is zero or an integer selected from 1-8 or greater than 9. For example, x may be 0, 1, 2, 3, 4, 5, 6, 7, 8, 10, 11, 12, 13, 14, or 15. In certain preferred embodiments, x is selected from 3, 4, 5, 6, 7, 8, 10, 11, and 12.

In some embodiments, the methods of insect control according to the invention involve compounds having the structure of formula (III)

wherein R is $C_1$-$C_{12}$ alkyl. For example, R may be methyl, ethyl, propyl, butyl, pentyl, hexyl, and the like. In certain preferred embodiments, R is methyl or ethyl.

According to the invention, there is provided the use of blends of at least two compounds having the structure of formulae (I), (II) and/or (III) to provide enhanced attraction of mosquitoes and other blood-feeding insects.

The compositions of the invention comprise at least two compounds selected from compounds having the structure of formulae (I), (II), and (III). In some embodiments, the compositions have exactly two such compounds. In other embodiments, the compositions have up to 8 such compounds. In some embodiments, the compositions have exactly 3, or exactly 4, or exactly 5, or exactly 6, or exactly 7, or exactly 8 such compounds. In some embodiments, the compositions consist of compounds having structures selected from exactly two of formulae (I), (II), and (III). In other embodiments, the compositions consist of compounds having structures selected from exactly one of formulae (I), (II), and (III). In still other embodiments, the compositions consist of compounds having structures selected from all three of formulae (I), (II), and (III). In some embodiments, the compositions include no compounds that are insect repellant in isolation.

As an example, a series of preferred attractant compositions can be prepared using between two and eight compounds selected from isobutyric acid, isovaleric acid, octanal, nonanal, decanal, dodecanal, and tridecanal and 2-methylphenol. The active compounds are mixed in varying amounts, and tested for insect attractiveness using the methods described herein. In some compositions, the mixture of active compounds is combined with VASELINE® or another additive prior to use. For example, a composition is prepared using isobutyric acid and isovaleric acid as active compounds. A series of such compositions is prepared, using ratios that range from 100:1 to 1:100 (isobutyric acid to isovaleric acid), and include such ratios as 10:1, 5:1, 3:1, 2:1, 1:1, 1:2, 1:3, 1:5, and 1:10. Similarly, a series of compositions may be prepared using isobutyric acid, isovaleric acid, and octanal as active compounds. As with the 2-component compositions, a three-component composition can be prepared using similar ratios of active agents. Similarly, a series of compositions may be prepared using isobutyric acid, isovaleric acid, octanal, and nonanal as active compounds. Similarly, a series of compositions may be prepared using isobutyric acid, isovaleric acid, octanal, nonanal, and decanal as active compounds. Similarly, a series of compositions may be prepared using isobutyric acid, isovaleric acid, octanal, nonanal, decanal, and dodecanal as active compounds. Similarly, a series of compositions may be prepared using isobutyric acid, isovaleric acid, octanal, nonanal, decanal, dodecanal, and tridecanal as active compounds. Similarly, a series of compositions may be prepared using isovaleric acid and octanal as active compounds. Similarly, a series of compositions may be prepared using isovaleric acid, octanal, and nonanal as active compounds. Similarly, a series of compositions may be prepared using isovaleric acid, octanal, nonanal, and decanal as active compounds. Similarly, a series of compositions may be prepared using isovaleric acid, octanal, nonanal, decanal, and dodecanal as active compounds. Similarly, a series of compositions may be prepared using isovaleric acid, octanal, nonanal, decanal, dodecanal, and tridecanal as active compounds. Similarly, a series of compositions may be prepared using octanal and nonanal as active compounds. Similarly, a series of compositions may be prepared using octanal, nonanal, and decanal as active compounds. Similarly, a series of compositions may be prepared using octanal, nonanal, decanal, and dodecanal as active compounds. Similarly, a series of compositions may be prepared using octanal, nonanal, decanal, dodecanal, and tridecanal as active compounds. Similarly, a series of compositions may be prepared using nonanal and decanal as active compounds. Similarly, a series of compositions may be prepared as described above using nonanal, decanal, and dodecanal as active compounds. Similarly, a series of compositions may be using nonanal, decanal, dodecanal, and tridecanal as active compounds. Similarly, a series of compositions may be prepared using decanal and dodecanal as active compounds. Similarly, a series of compositions may be prepared using decanal, dodecanal, and tridecanal as active compounds. Similarly, a series of compositions may be prepared using dodecanal and tridecanal as active compounds. Similarly, a series of compositions may be prepared using all eight of the active compounds. The skilled artisan will appreciate that other combinations of the compounds are also prepared as described. In each of the compositions, the amount of each active compound may be selected to mimic the relative amounts found in natural human foot odours (either for an average population or for the foot odour of a select individual). Alternatively, the amount of each active compound may be modified (from the amounts in natural human foot odours) such that the compositions have maximal insect attractiveness as measured by the methods described herein. Each of the compositions may be further combined with an additive such as acetone, and/or an additional active compound such as 1-octen-3-ol, lactic acid, 7-octenoic acid, etc. Each of the compositions may be further combined with a controlled-release $CO_2$ composition.

The compositions of the invention may further comprise one or more additional active compounds, also referred to herein as secondary insect attractant compounds. Such compounds may be either synthetic or naturally occurring, and need not be naturally associated with animal odours. In some preferred embodiments, additional active compounds are naturally occurring compounds that are found in human odours. Such odours include compositions found on the skin and hair such as sweat and compositions released during respiration. Examples of such compounds include carbon dioxide, acetone, 1-octen-3-ol, ammonia, lactic acid, 7-octenoic acid, 2-oxopentanoic acid, geometric isomers of 3-methyl-2-hexenoic acids, and fatty acids, such as those associated with the activity of microflora on animal skin.

The compounds described herein may be obtained by any appropriate method, including synthetic preparation, isolation from natural sources, or any combination thereof. For compounds obtained via synthetic preparation, the compounds may be prepared using synthetic methods and standard procedures that are known to those skilled in the art of synthetic organic chemistry and used for the preparation of analogous compounds. Appropriate synthetic procedures may be found, for example, in J. March, *Advanced Organic Chemistry: Reactions, Mechanisms and Structure,* 5th Edition (New York: Wiley-Interscience, 2001). In addition, chiral active agents may be in isomerically pure form, or they may be used as a racemic mixture of isomers.

The compositions of the invention may be prepared by any appropriate method. In some preferred methods, the active compounds of the composition are mixed along with one or more of the additives described herein to form a composition suitable for application (e.g. to the environment, or to a substrate) as desired. The order of mixing the compounds and additives is generally not limited in any manner. In other preferred methods, the active compounds are mixed, and the mixture is used directly without including other additives.

The compounds of the compositions of the invention, as well as the relative proportions of such compounds, may be selected according to any of the criteria described herein. For example, the compounds and relative amounts may be selected such that the compositions have maximally enhanced insect-attractive properties (as measured, for example, by the methods disclosed herein, or by any other appropriate method) for blood-feeding insects such as mosquitoes, particularly *An. gambiae*. As another example, the compounds and amounts, and any methods by which the are administered, may be selected to control the rate of release of the attractant compositions. It will be appreciated that, in some embodiments, a constant release rate (i.e. zero-order kinetics) at an optimized rate is desirable. It will further be appreciated, however, that the active compounds and additives may be selected to obtain a desired release rate suitable for the particular ecological conditions of the intended application.

In some embodiments, the compositions described herein comprise only active compounds (i.e., no additives). In other embodiments, other ingredients (e.g., additives such as those described in more detail herein below) are present, and the amount of active compounds in the composition typically ranges from about 0.05 wt % to about 99 wt % based on the total weight of the composition. For example, the overall amount of active compounds may range from about 0.05 wt % to about 50 wt %, or from about 0.1 wt % to about 25 wt %. As mentioned previously, the ratio of active compounds in a composition containing two active compounds may range from 1:1 to 100:1, but is more preferably in the range of 1:1 to 10:1. Similarly, such ratios apply between any two active compounds when more than two active compounds are included. In one embodiment, the weight percentages of the active compounds in a formulation according to the invention are selected to mirror the weight percentages of the compounds found in natural animal odours. For example, a composition may comprise the following eight compounds in weight percentages that correspond to natural human foot odours, as indicated: isobutyric acid (1%); isovaleric acid (2%); octanal (1.5%); nonanal (24%); decanal (62%); dodecanal (4%); tridecanal (3.8%); and 2-methylphenol (1.6%). In other embodiments, the weight percentages may be varied from those of the natural animal odours. For example, similar compositions can be prepared using the compounds in the following weight percent ranges: isobutyric acid (0.5-2%); isovaleric acid (1-3%); octanal (1-3%); nonanal (15-35%); decanal (30-75%); dodecanal (2-8%); tridecanal (2-8%); and 2-methylphenol (1-3%)

In addition to the active compounds described previously, it may be necessary or desirable in some cases (depending, for instance, on the particular composition or method of use) to incorporate any of a variety of additives, e.g., compounds that improve shelf-life, solubility, dispersive ability, etc. Suitable additives include acids, antioxidants, antimicrobials, bases, buffers, carriers, colorants, crystal growth inhibitors, defoaming agents, diluents, emollients, fillers, gelling agents, fragrances, lubricants, propellants, thickeners, salts, solvents, surfactants, UV screens, other chemical stabilizers, and mixtures thereof. Examples of these additives can be found, for example, in M. Ash and I. Ash, *Handbook of Pharmaceutical Additives* (Hampshire, England: Gower Publishing, 1995), the contents of which are herein incorporated by reference. Additives may be added for convenience of use, or for protection of the active agents and enhancement of the duration of their effectiveness. For example, additives such as antioxidants may be specifically included to minimize oxidative or photochemical breakdown of constituents.

In one preferred embodiment, a composition is provided that comprises from 2 to 8 compounds having structures selected from formulae (I), (II), and (III), and further comprises a carrier that is different from any compound found in human sweat or a carrier that is different from any compound produce by the action of microflora on human skin.

The compositions of the invention may be in the form of liquid compositions, including solutions, suspensions, and emulsions. Solutions may be aqueous solutions of the active compounds and may include one or more of propylene glycol, polyethylene glycol, and the like. Aqueous suspensions can be made by dispersing the finely divided active agent in water with viscous material, such as natural or synthetic gums, resins, methylcellulose, sodium carboxymethylcellulose, petroleum jelly, VASELINE®, and other suspending agents. Alternatively, solutions may be non-aqueous organic solvent-based. Also included are compositions of solid form which are intended to be converted, shortly before use, to liquid form.

The chemical compositions according to the invention may be formulated as ointments, creams or lotions. Such compositions are useful, for example, for topical application to the epidermis (e.g., of a human subject), or for application in insect traps targets, and the like. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Aerosol compositions suitable for insect control include, for example, compositions wherein the active compound is provided in a pressurized pack with a suitable propellant. Suitable propellants include chlorofluorocarbons (CFCs) such as dichlorodifluoromethane, trichlorofluoromethane, or dichlorotetrafluoroethane, carbon dioxide, or other suitable gases. The aerosol may also contain a surfactant such as lecithin.

Suitable dry powders include, for example, a powder mix of the compounds in a suitable powder base such as lactose, starch, starch derivatives such as hydroxypropylmethyl cellulose and polyvinylpyrrolidone (PVP). The active compounds may be adsorbed onto a powder base.

Furthermore, the invention includes all controlled-release compositions and devices prepared for convenience and/or for extending the duration of performance of the individual constituents in the blends used as baits to attract insects.

In some embodiments, the invention provides a method for preparing an insect attractant composition comprising selecting at least two compounds found naturally in human odours. For example, the compounds may be found in human foot odour. Such compounds may, for example, have a structure according to any of formulae (I), (II), and (III) as described herein. As described herein, a relative amount is selected for each compound, and the compounds are combined in the amounts selected to provide an insect attractant composition. The insect attractive composition is used in a method for controlling the behaviour of insects, also as described herein.

The insect-attractant compositions may be delivered to, and used in, an environment in which insect control is desired. Any appropriate method may be used for supplying the compositions to such environments. For example, insect-attractant compositions may be disposed on a substrate, or dispersed in the environment as a liquid, mist, vapor, or the like. Suitable substrates include, for example, natural or synthetic fabric cloths, netting, and the like. Compositions may be used in traps or insecticide-treated targets.

The compositions of the invention may be used in insect control systems that integrate them with other insect control tactics. For example, the compositions may be used in conjunction with insect-repellant compositions in a "push-pull" approach. Such an approach uses an insect repellant composition and an insect-attractive composition to direct insects away from one particular region or location and towards another particular region or location. For example, space protection may involves fumigation of human dwellings with controlled-release repellent compositions to provide the 'push' effect in the 'push-pull' strategy for more effective suppression of insect populations. As a further example, the compositions may be used in methods of insect control that involve personal protection, such as repellent compositions or insecticide-treated bed-nets.

In one aspect, the compositions of the invention are used in conjunction with an insect repellant formulation comprising one or more compounds selected from: (a) compounds having the structure of formula (IV)

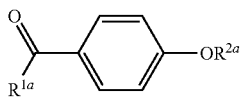

(IV)

wherein $R^{1a}$ and $R^{2a}$ are independently $C_1$-$C_{24}$ alkyl; (b) compounds having the structure of formula (V)

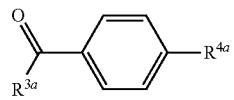

(V)

wherein $R^{3a}$ and $R^{4a}$ are independently $C_1$-$C_{24}$ alkyl; and (c) compounds having the structure of formula (VI)

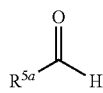

(VI)

wherein $R^{5a}$ is a linear 10-carbon alkyl chain which may be substituted or unsubstituted. Preferred substituents are lower alkyl substituents, including methyl, ethyl, n-propyl, isopropyl, n-butyl, isobutyl, t-butyl, pentyl, and hexyl, as well as other alkyl substituents including octyl, decyl, cyclopentyl, and cyclobutyl. For example, $R^{1a}$ and $R^{2a}$ may be linear or branched alkyl. In some embodiments, $R^{1a}$ and $R^{2a}$ are independently lower alkyl. Further for example, in some embodiments, $R^{1a}$ and $R^{2a}$ are selected from ethyl and methyl. Further for example, $R^{3a}$ and $R^{4a}$ may be linear or branched alkyl. In some embodiments, $R^{3a}$ and $R^{4a}$ are independently lower alkyl. Further for example, in some embodiments, $R^{3a}$ and $R^{4a}$ are selected from ethyl and methyl. The insect repellant formulations may comprise 2, 3, 4, or 5 compounds selected from formulae (IV), (V), and (VI), and may further comprise one or more additives such as those described herein. Compounds associated with natural human foot odours include both insect attractant and insect repellant compounds. Accordingly, particularly preferred insect repellant compositions for use in conjunction with the insect attractant formulations described herein are those that comprise one or more insect repellant compounds having the structure of formula (IV), (V), or (VI), wherein such compounds are natural components of human foot odours.

The methods and compositions described herein may be used to decrease the total population of insects in an environment. For example, the compositions may be used to sequester the insects in traps, targets, and the like. Alternatively or in addition, the compositions may be used in conjunction with one or more insecticides, in which case population control is achieved by killing insects that are attracted to the compositions of the invention. Mass trapping and control of mosquitoes with baited traps treated with chemo- or bio-pesticides can be enhanced using the insect-attractive compositions of the invention. Alternatively or in addition, insect copulation control in a target environment may be achieved by releasing insect attractant compositions in neighboring environments, thereby drawing the insects out of the target environment. The compositions of the invention can also be used in enhancing the sensitivity of tools (e.g., traps) used in spatial and temporal sampling of the disease vectors. Such sampling may be required for better understanding of the disease dynamics and for facilitating strategic interventions to control mosquitoes and/or treat diseases they transmit.

Insects that may be the target of control using the compositions of the invention include blood-feeding insects such as mosquitoes, muscids, tabanids, tachanids, tsetse, black flies, ticks, and the like. In one example, the compositions of the invention are used to control the population of malaria vectors including *Anopheles* mosquitoes (e.g., *An. gambiae* Giles complex and *An. funestus* Giles). Insect population control using the compositions and methods according to the invention may be employed for controlling the spread of diseases such as malaria and other insect-borne diseases. It will be appreciated that the compositions and methods of the invention may be used in conjunction with other methods of controlling insect populations and behavior not specifically mentioned herein.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

It is to be understood that while the invention has been described in conjunction with the preferred specific embodiments thereof, that the foregoing description as well as the examples that follow, are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains.

EXAMPLES

Example 1

Comparison of Mosquito Catches by Traps Baited with a Synthetic Blend and with a Light Trap Preparation of Attractant Formula.

An attractive human foot odour was obtained, and a synthetic blend was prepared using eight constituents that were found in the natural odour. The proportions of the eight constituents in the synthetic blend were equal to the relative proportions found in the natural foot odor. The constituents and amounts (% weight) were: isobutyric acid (1%); isovaleric acid (2%); octanal (1.5%); nonanal (24%); decanal (62%); dodecanal (4%); tridecanal (3.8%); and 2-methylphenol (1.6%).

Testing Procedure for Attractant Formula.

The average catches of a counter flow geometry (CFG) trap (American Biophysics Corporation) baited with a synthetic blend of eight constituents that make up the attractive mixture of human foot odours (i.e. isobutyric acid, isovaleric acid, octanal, nonanal, decanal, dodecanal, tridecanal, and 2-methylphenol) were compared with those of a CDC (Center for Disease Control, USA) light trap used widely in mosquito monitoring. Each comparison was performed repeatedly between 20:00 hrs in the night and 06:00 hrs the following morning under semi-field conditions in a screenhouse (11.5×7.1×3.0 m) at Mbita Point on the shores of Lake Victoria in Kenya. The two traps in each test were located at the corners of the screenhouse and were interchanged before each replicate. 200 starved laboratory-reared female *An. gambiae* s.s. were released from a cup placed at the center between the two traps being compared and the number of mosquitoes caught in each trap counted. The relative catch sizes of each pair of traps were computed and analysed statistically.

Results.

The CFG trap baited with the odour blend was much more effective (P<0.0001; t-Test) in trapping mosquitoes with an average (±SE) of 129.0±9.7 compared with 23.5±11.6 caught in the CFG trap.

Example 2

Comparison of Mosquito Catches in Traps Baited with a Synthetic Blend and a Human Volunteer The average catches of a counter flow geometry (CFG) trap (American Biophysics Corporation) baited with the synthetic blend prepared in Example 1 was compared with those of a bed-net trap [Mathenge et al. (2002), *Medical and Veterinary Entomology*, 16, 1-8] a human-baited exposure-free trap, also referred to as 'Mbita trap'. Each comparison was performed repeatedly between 20:00 hrs in the night and 06:00 hrs the following morning under semi-field conditions in a screenhouse (11.5×7.1×3.0 m) also at Mbita Point on the shores of Lake Victoria. The two types of traps in each test were located at the corners of the screenhouse and were interchanged before each replicate. 200 starved laboratory-reared female *An. gambiae* s.s. were released from a cup placed at the center between the two traps being compared and the number of mosquitoes caught in each trap counted. The relative catch sizes of each pair of traps were computed and analysed statistically.

Results:

The CFG trap baited with the synthetic odour blend caught significantly more (P<0.01; t-Test) mosquitoes with an average (±SE) of 105.3±14.5 compared with 45.5±5.6 in the bed-net trap.

Example 3

Comparison of the Performance of a Blend of 8 Compounds with Complete Foot Odour Number of wild mosquitoes trapped in pairs of CFG traps baited with fresh cotton socks either (i) treated with 1 g of 10% blend of 8 compounds (i.e. isobutyric acid (1%); isovaleric acid (2%); octanal (1.5%); nonanal (24%); decanal (62%); dodecanal (4%); tridecanal (3.8%); and 2-methylphenol (1.6%)) in Vaseline, or (ii) worn for 12 hours by a selected individual, were compared in a human dwelling in Lwanda, Suba District, in Kenya. In an earlier series of tests with foot odours collected from 16 persons, the selected individual was consistently found to be one of two with the most attractive natural foot odour (8-fold more attractive than the least attractive foot odour). The tests were conducted in a 12×8 ft room with a bed occupied by the owner of the household who volunteered to participate in the experiment. Every evening two traps, one freshly baited with socks treated with the test blend in Vaseline and the other freshly collected from the individual, were placed diagonally in the room. The positions of the two traps were interchanged every evening. The number of mosquitoes entering the room from its natural habitat around the dwelling caught in each trap was counted, their relative catch sizes computed and analysed statistically.

Results:

CFG traps baited with the synthetic 8-compound blend caught significantly more number of mosquitoes (P<0.05; t-Test), with an average of 35.5±5.7 compared with 19.5±4.2 in the trap with socks baited with the full natural foot odour, indicating greater potency of the synthetic blend even in the natural human dwelling.

Example 4

Use of "Push-Pull" Method for Mosquito Control

A group of houses located in an environment with a natural mosquito population is subjected to controlled indoor fumigation using a mosquito repellant composition. Concurrently, traps baited with an attractant composition (prepared as described in the previous Examples) are placed in outdoor locations around the periphery of the group of houses to attract the mosquitoes.

What is claimed is:

1. A composition for modifying insect behaviour comprising exactly 3, 4, 5, 6, 7, or 8 insect attractant compounds selected from: (a) compounds having the structure of formula (I)

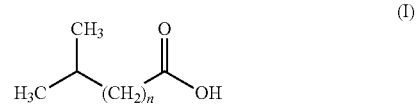

wherein n is zero or an integer;

(b) compounds having the structure of formula (II)

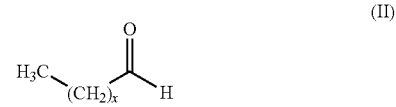

wherein x is zero or an integer selected from 1-8 or greater than 9; and (c) compounds having the structure of formula (III)

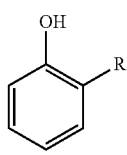

wherein R is $C_1$-$C_{12}$ alkyl, wherein a compound from each of formulae (I), (II), and (III) is present in the composition.

2. The composition of claim 1, wherein the composition is attractive to *Anopheles gambiae*.

3. The composition of claim 1, wherein n is 0 or 1; x is 6, 7, 8, 10, or 11; and R is methyl.

4. The composition of claim 1, wherein the composition does not contain any insect-repellant compounds.

5. The composition of claim 1, wherein the composition further contains one or more additives selected from acids, antioxidants, antimicrobials, bases, buffers, carriers, colorants, crystal growth inhibitors, defoaming agents, diluents, emollients, fillers, gelling agents, fragrances, lubricants, propellants, thickeners, salts, solvents, surfactants, UV screens, other chemical stabilizers, and mixtures thereof.

6. The composition of claim 1, comprising: isobutyric acid, isovaleric acid, octanal, nonanal, decanal, dodecanal, tridecanal, 2-methylphenol, and a carrier.

7. The composition of claim 1, wherein the composition does not contain any insect-repellant compounds having the structure of formula (IV)

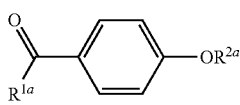

wherein $R^{1a}$ and $R^{2a}$ are independently $C_1$-$C_{24}$ alkyl.

8. The composition of claim 1, wherein the composition does not contain any insect-repellant compounds having the structure of formula (V)

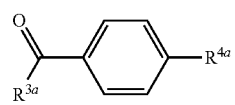

wherein $R^{3a}$ and $R^{4a}$ are independently $C_1$-$C_{24}$ alkyl.

9. The composition of claim 1, wherein the composition does not contain any insect-repellant compounds having the structure of formula (VI)

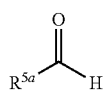

wherein $R^{5a}$ is a linear $C_{10}$ alkyl chain which may be substituted or unsubstituted.

10. The composition of claim 1, wherein n is 0 or 1, and wherein the composition has exactly 8 compounds selected from compounds having the structure of formulae (I), (II), and (III).

11. The composition of claim 1, wherein x is 6, 7, 8, 10, or 11, and wherein the composition has exactly 8 compounds selected from compounds having the structure of formulae (I), (II), and (III).

12. The composition of claim 1, wherein R is methyl, and wherein the composition has exactly 8 compounds selected from compounds having the structure of formulae (I), (II), and (III).

13. A composition for modifying insect behaviour comprising exactly eight insect attractant compounds selected from: (a) compounds having the structure of formula (I)

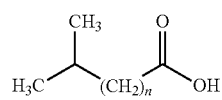

wherein n is zero or an integer;
(b) compounds having the structure of formula (II)

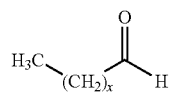

wherein x is zero or an integer selected from 1-8 or greater than 9; and
(c) compounds having the structure of formula (III)

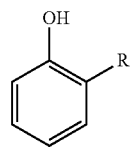

wherein R is $C_1$-$C_{12}$ alkyl,
and further wherein: n is 0 or 1; x is 6, 7, 8, 10, or 11; or R is methyl.

14. A method for preparing the composition of claim 1, the method comprising selecting at least three compounds found in human odours, selecting a relative amount for each compound, and combining the compounds in the amounts selected to provide an insect attractant composition, wherein the compounds are selected from compounds having the structure of formula (I), formula (II), and formula (III).

15. The method of claim 14, further comprising adding to the composition one or more secondary insect attractive compounds.

16. The method of claim 15, wherein the one or more secondary insect attractive compounds is selected from carbon dioxide, acetone, 1-octene-3-ol, 7-octenoic acid, ammonia, 2-oxopentanoic acid, 3-methyl-2-hexenoic acid, fatty acids, and lactic acid.

17. The method of claim 14, wherein the insect attractive composition is attractive to one or more blood-feeding insects selected from mosquitoes, muscids, tabanids, tachanids, tsetse flies, black flies, and ticks.

18. A method for controlling the behaviour of insects, the method comprising: supplying the composition of claim 1 to an environment containing insects, wherein the composition controls the behaviour of the insects.

19. The method of claim 18, wherein the composition further comprises one or more secondary insect attractant compounds.

20. The method of claim 18, wherein the method further comprises supplying to the environment an insect-repellant compound.

21. The method of claim 18, wherein the composition, when placed in an environment containing both mosquitoes and a control composition, attracts more mosquitoes over a predetermined period of time than the control composition.

* * * * *